US010925934B2

(12) United States Patent
Sullivan et al.

(10) Patent No.: US 10,925,934 B2
(45) Date of Patent: Feb. 23, 2021

(54) SPRAY DRIED MYROSINASE AND USE TO PRODUCE ISOTHIOCYNATES

(75) Inventors: Richard C. Sullivan, Louisville, KY (US); Joseph A. Lyons, Jeffersontown, KY (US); Sanford D. Caudill, Louisville, KY (US); Kean Ashurst, Taylorsville, KY (US)

(73) Assignee: Caudill Seed and Warehouse Co., Inc., Louisville, KY (US)

( * ) Notice: Subject to any disclaimer, the term of this patent is extended or adjusted under 35 U.S.C. 154(b) by 1100 days.

(21) Appl. No.: 13/401,956

(22) Filed: Feb. 22, 2012
(Under 37 CFR 1.47)

(65) Prior Publication Data

US 2012/0213890 A1    Aug. 23, 2012

Related U.S. Application Data

(60) Provisional application No. 61/445,156, filed on Feb. 22, 2011.

(51) Int. Cl.
| A23L 1/28 | (2006.01) |
| A61K 38/47 | (2006.01) |
| A23L 29/00 | (2016.01) |
| A23L 33/15 | (2016.01) |
| A61K 36/31 | (2006.01) |

(52) U.S. Cl.
CPC .............. *A61K 38/47* (2013.01); *A23L 29/06* (2016.08); *A23L 33/15* (2016.08); *A61K 36/31* (2013.01)

(58) Field of Classification Search
CPC ......... A61K 36/31; A61K 38/47; A23L 29/06; A23L 33/15
USPC ..................................................... 426/61, 49
See application file for complete search history.

(56) References Cited

U.S. PATENT DOCUMENTS

| 3,493,652 A | 2/1970 | Hartman |
| 4,083,836 A | 4/1978 | Anjou et al. |
| 5,043,178 A | 8/1991 | Gottesman et al. |
| 5,077,071 A | 12/1991 | Strop |
| 5,686,108 A | 11/1997 | Pusateri et al. |
| 5,725,895 A | 3/1998 | Fahey et al. |
| 5,834,043 A | 11/1998 | Van Den Berg et al. |
| 5,882,646 A | 3/1999 | Pusateri et al. |
| 5,968,505 A * | 10/1999 | Fahey et al. ................ 424/94.1 |
| 5,968,567 A | 10/1999 | Fahey et al. |
| 6,010,717 A * | 1/2000 | Arends-Scholte ... A61K 9/2059 424/464 |
| RE36,784 E | 7/2000 | Cho et al. |
| 6,086,936 A | 7/2000 | Wilson et al. |
| 6,117,460 A | 9/2000 | Kortschack |
| 6,177,122 B1 | 1/2001 | Fahey et al. |
| 6,242,018 B1 | 6/2001 | Fahey et al. |
| 6,348,220 B1 | 2/2002 | Ribnicky et al. |
| 6,361,812 B1 | 3/2002 | Ekanayake et al. |
| 6,436,450 B1 * | 8/2002 | Omary .................... A23L 19/01 424/755 |
| 6,521,818 B1 | 2/2003 | Fahey |
| 6,737,441 B2 | 5/2004 | Fahey |
| 6,812,248 B2 | 11/2004 | Zhang et al. |
| 6,824,796 B2 | 11/2004 | Pusateri et al. |
| 7,105,190 B2 | 9/2006 | Ekanayake et al. |
| 7,303,770 B2 | 12/2007 | Fahey et al. |
| 7,371,419 B1 | 5/2008 | West et al. |
| 7,402,569 B2 | 7/2008 | Fahey |
| 7,407,986 B2 | 8/2008 | Gao et al. |
| 7,744,937 B2 | 6/2010 | West et al. |
| 7,879,822 B2 | 2/2011 | Dagan et al. |
| 2002/0015722 A1 | 2/2002 | Herzog et al. |
| 2002/0034543 A1 * | 3/2002 | Kirschner ............ A61K 9/0056 424/465 |
| 2002/0090405 A1 | 7/2002 | Guthrie et al. |
| 2002/0147155 A1 | 10/2002 | Foster et al. |
| 2003/0091518 A1 | 5/2003 | Pauly et al. |
| 2003/0138936 A1 * | 7/2003 | Mizuguchi ............... C12N 1/04 435/252.31 |
| 2003/0180352 A1 | 9/2003 | Patel et al. |
| 2003/0194455 A1 | 10/2003 | Taylor |
| 2003/0235634 A1 | 12/2003 | Pusateri et al. |
| 2004/0001817 A1 | 1/2004 | Giampapa |
| 2004/0052879 A1 | 3/2004 | Ravagnan et al. |
| 2004/0133936 A1 | 7/2004 | Rossiter et al. |

(Continued)

FOREIGN PATENT DOCUMENTS

| CN | 101332295 A | 12/2008 |
| DE | 19649952 | 6/1998 |

(Continued)

OTHER PUBLICATIONS

NPL Yen G-C et al. J. Sci. Food Agric. 61: 471-475, 1993.*
NPL "Broccoli seed" retrieved on Feb. 3, 2014.*
NPL Chauhan et al. (Year: 2003).*
NPL Dobry et al. (in A model Based Methodology for Spray-drying Process Development , J Pharm Innov. 4: pp. 133-142, 2009). (Year: 2009).*
Bones, A.M., et al., "The myrosinase-glucosinolate system, its organization and biochemistry", Physiologia Plantarum, 97:194-208, 1996, Denmark.
Burmeister, W.P., et al., "High Resolution X-ray Crystallography Shows That Ascorbate is a Cofactor for Myrosinase and Substitutes for the Function of the Catalytic Base", The Journal of Biological Chemistry, 275(50):39385-39393, Dec. 15, 2000.

(Continued)

*Primary Examiner* — Erik Kashnikow
*Assistant Examiner* — Bhaskar Mukhopadhyay
(74) *Attorney, Agent, or Firm* — Dentons Bingham Greenebaum LLP; Brian W. Chellgren

(57) ABSTRACT

A spray dried myrosinase/ascorbate mixture is formed from the steps comprising: providing a source of myrosinase, adding ascorbate to the source of myrosinase, heating the source of myrosinase to a temperature of about 104° F. (about 40° C.) or higher, and spray drying the myrosinase/ascorbate mixture. The spray dried myrosinase/ascorbate mixture may be used to prepare isothiocyanates. The spray dried myrosinase/ascorbate mixture may also be mixed with glucoraphanin and used in an activated tablet or capsule.

4 Claims, No Drawings

(56) References Cited

U.S. PATENT DOCUMENTS

| | | | |
|---|---|---|---|
| 2005/0031768 | A1 | 2/2005 | Sakai et al. |
| 2005/0042347 | A1 | 2/2005 | Bathurst et al. |
| 2005/0055744 | A1 | 3/2005 | Quiros et al. |
| 2005/0123560 | A1 | 6/2005 | Sinnott |
| 2006/0003073 | A1 | 1/2006 | Etzel et al. |
| 2006/0020046 | A1 | 1/2006 | Goralczyk et al. |
| 2006/0127996 | A1* | 6/2006 | Fahey .................. A23L 2/52 435/128 |
| 2007/0031581 | A1 | 2/2007 | West et al. |
| 2007/0033675 | A1 | 2/2007 | Barten |
| 2007/0190080 | A1 | 8/2007 | Friedman |
| 2007/0190209 | A1 | 8/2007 | Sinnott |
| 2008/0107792 | A1 | 5/2008 | Verhoeyen et al. |
| 2008/0311192 | A1* | 12/2008 | West .................. A61K 9/1652 424/463 |
| 2009/0081138 | A1 | 3/2009 | Ashurst |
| 2012/0135468 | A1 | 5/2012 | Katase et al. |
| 2013/0089640 | A1 | 4/2013 | Lohscheidt et al. |

FOREIGN PATENT DOCUMENTS

| | | |
|---|---|---|
| DE | 10308298 | 9/2004 |
| DE | 102005033616 | 1/2007 |
| EP | 0006654 | 1/1980 |
| EP | 0668026 | 8/1995 |
| EP | 1752052 | 2/2007 |
| EP | 2213280 | 8/2010 |
| JP | H04-72137 | 3/1992 |
| JP | 2000-166549 A | 6/2000 |
| JP | 2002-191323 A | 7/2002 |
| JP | 2004-514456 A | 5/2004 |
| JP | 2005206495 | 8/2005 |
| JP | 2009-529324 A | 8/2009 |
| WO | WO 1995/008275 | 3/1995 |
| WO | WO 1999/007240 | 2/1999 |
| WO | WO 1999/020242 | 4/1999 |
| WO | WO 2000/001222 | 1/2000 |
| WO | WO 2000/004785 | 2/2000 |
| WO | WO 2000/030604 | 6/2000 |
| WO | WO 2000/061163 | 10/2000 |
| WO | WO 2001/091764 | 12/2001 |
| WO | WO 2002/45527 A2 | 6/2002 |
| WO | WO 2003/051313 | 6/2003 |
| WO | WO 2004/060402 | 7/2004 |
| WO | WO 2004/073418 | 9/2004 |
| WO | WO 2005/013722 | 2/2005 |
| WO | WO 2006/012213 | 2/2006 |
| WO | WO 2006/102236 | 9/2006 |
| WO | WO 2007/094827 | 8/2007 |
| WO | WO 2010/140435 A1 | 12/2010 |

OTHER PUBLICATIONS

Burmeister, W.P., et al., "The crystal structures of Sinapis alba myrosinase and a covalent glycosyl-enzyme intermediate provide insights into the substrate recognition and active-site machinery of an S-glycosidase", Structure, 5:663-675, May 15, 1997.

Ettlinger, M.G., et al., "Vitamin C as a Coenzyme: The Hydrolysis of Mustard Oil Glucosides", Chemistry: Ettlinger et al., Proc. N.A.S., 47:1875-1880, 1961.

Kliebenstein, Dan J., Kroymann, Juergen, and Mitchell-Olds, Thomas, "The glucosinolate-myrosinase system in an ecological and evolutionary context", Mar. 25, 2005, pp. 264-271, vol. 8, Current Opinion in Plant Biology, US.

Matisheski, Nathan V., Juvik, John A., Jeffery, Elizabeth H., "Heating decreases epithiospecifier protein activity and increases sulforaphane formation in broccoli", May 19, 2004, pp. 1273-1281, vol. 65, Phytochemistry, US.

Botti M. Grazia, Taylor, Malcolm G., and Butting, Nigel P., "Studies on the Mechanism of Myrosinase", May 24, 1995, pp. 20530-20535, vol. 270, No. 35, The Journal of Biological Chemistry, US.

Kim, Moo Jung, "Sulforaphance, an Anticarcinogen in Broccoli", Oct. 11, 2007, Vegetable Science Lab.

Chinese Office Action dated Jul. 7, 2014 for Application No. CN 201280014757.5.

International Preliminary Report on Patentability dated Aug. 27, 2013 for Application No. PCT/US2012/026036.

Japanese Office Action, Preliminary Notice of Reasons for Rejection, dated Feb. 9, 2016 for Application No. JP 2013-55512, 6 pgs.

Kleinwachter, M., et al., "A novel approach for reliable activity determination of ascorbic acid depending myrosinases," J. Biochem. Biophys. Methods, 2004, 59:253-265, 13 pgs.

Ludikhuyze, L., et al., "The Activity of Myrosinase from Broccoli (Brassica oleracea L. cv. Italica): Influence of Intrinsic and Extrinsic Factors," Journal of Food Protection, 2000, 63(3):400-403, 4 pgs.

U.S. Appl. No. 11/761,843, filed Jun. 12, 2007, West et al.

International Search Report and Written Opinion dated Apr. 26, 2012 for Application No. PCT/US2012/26036.

Defendant's Objections and Responses to Plaintiff's First Set of Interrogatories, Requests for the Production of Documents, and Requests for Admission; Caudill Seed and Warehouse Company, Inc. d/b/a Caudill Seed Company v. Kean H. Ashurst; Jefferson Circuit Court, Kentucky, Nov. 16, 2011. (See pp. 12-14, 21-22, 30-31, & 61-62.)

Information Disclosure Statement, filed Dec. 9, 2009 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (9 pages).

Notice of References Cited by Examiner, filled Sep. 14, 2011 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (2 pages).

Information Disclosure Statement, filed Feb. 21, 2012 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (page 2 of 2).

Information Disclosure Statement, filed Feb. 19, 2008 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (3 pages).

Notice of References Cited by Examiner, filed Jun. 19, 2009 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (1 page).

Information Disclosure Statement, filed Jul. 20, 2009 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (6 pages).

Notice of References Cited by Examiner, filed Aug. 6, 2009 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (1 page).

Notice of References Cited by Examiner, filed Mar. 7, 2012 for U.S. Appl. No. 11/761,843, produced with Kean H. Ashurst's Objections and Responses to Caudill Seed Company's First Set of Interrogatories, Requests for the Production of Documents, and Requests for Admission, Nov. 16, 2011. (1 page).

Badal, R., "Supercritical Carbon Dioxide Extraction of Lipids from Raw and Bioconverted Rice Bran", Thesis, Louisiana State University and Agricultural and Mechanical College, Dec. 2002.

Bjerg, B., et al., "Isolation of Intact Glucosinolates by Column Chromatography and Determination of Their Purity", Glucosinloates in Rapeseeds; Analytical Aspects, Oct. 1986, pp. 59-75, Martinus Nijhoff a member of the Kluwer Academic Publishers Group, Belgium.

(56) References Cited

OTHER PUBLICATIONS

Bones, A., et al., "The myrosinase-glucosinolate system, its organisation and biochemistry", Physiologia Plantarum, 1996, pp. 97:194-208.
Borgen, B., "Functional Analysis of Plant Idioblasts (Myrosin Cells) and their role in Defense, Development and Growth", Thesis, Norwegian University of Science and Technology, 2002.
Botti, M., et al., "Studies on the Mechanism of Myrosinase, Investigation of the Effect of Glycosyl Accpetors on Enzyme Activity", The Journal of Biological Chemistry, Sep. 1, 1995, vol. 270, No. 35, pp. 20530-20535.
Cheftel, J., "Hautes Pressions, Inactivation Microbiennè el Conservation des Aliments", C.R. Acad. Agric. FR., 1995, 81 (1), pp. 13-38.
Choi, S., et al., "D,L-Sulforaphane-induced cell death in human prostate cancer cells is regulated by inhibitor of apoptosis family proteins and Apaf-1", Carcinogenesis, 2007, vol. 28, No. 1, pp. 151-162.
Cortesi, R., et al.,"Hydroxy propyl methyl cellulose phyhalate (HPMCP) microparticles for enteric delivery of glucosinolate drived products from Cruciferous vegetable," Minerva Biotechnologica, Italy, 2000, vol. 12, pp. 293-300.
DeSilva, F. et al., "Some Like It Hot, Some Like It Cold". Published in Water Quality Products Magazine, Aug. 2000, 4 pages.
Epstein, M.S., et al., "Determination of Phosphorus in Copper-Based Alloys Using Ion-Exchange Chromatography and Direct-Current Plasma Emission Spectrometry". Analytical Chemistry, 1987, 59 (24), 2872-2876.
Fahey, et al., "Broccoli sprouts: An exceptionally rich source of inducers of enzymes that protect against chemical carcinogens" 1997, Proceedings of the National Academy of Sciences, vol. 94, pp. 10367-10372.
Fahey, et al., "The chemical diversity and distribution of glucosinolates and isothiocyanates among plants", Photochemistry, 2001, vol. 56, pp. 5-51.
Fahey, et al. "Separation and Purification of Glucosinolates From Crude Plant Homogenates by High-Speed Counter-Current Chromatography", Journal of Chromatography A, 2003, vol. 996, pp. 85-93.
GE Healthcare/Sephadex Product Brochure. No Date, pp. 1-15.
Getahun, S., et al., "Conversion of Glucosinolates to Isothiocyanates in Humans after Ingestion of Cooked Watercress", Cancer Epidemiology, Biomarkers & Prevention, May 1999, vol. 8, pp. 447-451.
Gil, et al., "Degradation of glusinolates of Nasturtium officinale seeds". Photochemistry. 1980, vol. 19, pp. 1657-1660.
Gow-Chin, et al., "Myrosinase Activity and Total Glucosinolate Contect of Cruciferous Vegetable, and Some Properties of Cabbage Myrosinase in Taiwan", Journal of Science and Food Agriculture, 1993, vol. 61, pp. 471-475.
Hanley, et al., "Improved Isolation of Glucobrassicin and Other Glucosinolates", Journal of Science and Food Agriculture, 1983, vol. 34, pp. 869-873.
Hansen, M., et al., "Glucosinolates in Broccoli Stored Under Controlled Atmosphere." Journal of the American Society of Horticultural Science, col. 120, No. 6, 1995, pp. 1069-1074.
Hecht, et al., "Effects of watercress consumption on metabolism of a tobacco-specific lung carcinogen in smokers", Cancer Epidemiology, Biomarkers, & Prevention. Dec. 1995. vol. 4, pp. 877-884. (Abstract only).
Jeffrey, E., "Effect of processing on bioactives in vegetables: the case for more research on broccoli", University of Illinois at Urbana-Champaign.
Karovicova, et al., "The choice of strains of Lactobacillus species for the lactic acid fermentation of vegetable juices", European Food Research and Technology A, 1999, vol. 210, pp. 53-56. (Abstract only).
Kushad, M., et al., "Variation of Gluconsinolates in Vegetable Crops of Brassica oleracea". J. Agricultural Food Chemistry, 1999, 47, 1541-1548.

Kyung, K.H., et al., "Antimicrobial Activity of Sulfur Compounds Derived from Cabbage", Journal of Food Protection, vol. 60, No. 1, pp. 67-71.( Abstract only) , 1997.
Lenman, M., et al., "Differential Expression of Myrosinase Gene Families", Plant Physiol., 1993, pp. 103:703-711.
Letter from Richard Peet of Foley & Lardner LLP dated Apr. 18, 2008 to James P. Krueger of Fitch, Even, Tabin & Flannery regarding U.S. Patent Application Publication No. 2007/0031581 A1, copy to Antony Talalay (1 page).
Lewis, J., et al., "Glucosinolate Content of Brassica Vegetables: Analysis of Twenty-Four Cultivars of Calabrese." Food Chemistry, vol. 25, No. 4, 1987, pp. 259-268.
Liang, H., et al., "Effects of metal ions on myrosinase activity and the formation of sulforaphane in broccoli seed", Journal of Molecular Catalysts B: Enzymatic 43, 2006, pp. 19-22.
List, G.R., et al., "Supercritical CO2 Extraction and Processing of Oilseeds", Oil Mill Gazetteer, Dec. 1989, pp. 28-34.
Ludikhuyze, et al., "The Activity of Myrosinase form Broccoli: Influence of Intrinsic and Extrinsic Factors", 2000, Journal of Food Protection, vol. 63. No. 3, pp. 400-403.
Melia, C.D., et al., "Reivew Article: Mechanism of Drug Release from Tablets and Capsules, I: Disintegration." Alimentary Pharmacology & Therapeutics, 1989, vol. 3, pp. 223-232.
MetaCyc Pathway: glucosinolate breakdown, printed from http://biocyc.org/META/NEW-IMAGE?type=PATHWAY&object=PWY-5267&detail-level=3 on Apr. 5, 2011.
Mor-Mur, M. et al., "High-Pressure Processing Applied to Cooked Sausage Manufacture: Physical Properties and Sensory Analysis," Meat Science, 2003, 65, pp. 1187-1191.
NutraCea, Stabilized Rice Barn—Granular, Product Data Sheet, Effective May 31, 2010.
Palop, M.L., et al., "Degradation of sinigrin by Lactobacillus agilis strain R16", Food Microbiology, 1995, vol. 26, pp. 219-229. (Abstract Only).
Pang, K.S., "Physiological Modeling of the Small Intestine in Drug Absorption", Department of Pharmaceutical Sciences, University of Toronto, pp. 1-32.
Pereira, F.M.V., et al., "Influence of Temperature and Ontogeny of the Levels of Glucosinolates in Broccoli Sprouts and Their Effect on the Induction of mammalian Phase 2 Enzymes." Journal of Agricultural and Food Chemistry, vol. 50, No. 21, 2002, pp. 6239-6244.
Petri, N., et al., "Absorption/Metabolism of Sulforaphane and Quercetin, and Regulation of Phase II Enzymes, in Human Jejunum in Vivo", Drug Metabolism and Disposition, 2003, vol. 31, No. 6, pp. 31:805-813.
PolyLC Inc. HPLC Supplies for the Life Sciences, http://www.polyic.com/—accessed Nov. 25, 2008, 2 pages.
Riedl, M., et al., "Oral sulforaphane increases Phase II antioxidant enzymes in the human upper airway", Clinical Immunology, 2008.
Rochfort, S., et al., "The Isolation and Purification of Glucoraphanin From Broccoli Seeds by Solid Phase Extraction and Preparative High Performance Liquid Chromatography". Journal of Chromatography A, 2006, vol. 1120, pp. 205-210.
Shapiro, T., et al., "Safety, Tolerance, and Metabolism of Broccoli Sprout Glucosinolates and Isothiocyanates: A Clinical Phase I Study", Nutrition and Cancer, 2006, vol. 55, pp. 53-62.
Smith, et al., "Effects of Brassica vegetable juice on the induction of apoptosis and aberrant crypt foci in rat colonic mucosal crypts in vivo", 2003 Carcinogenesis, col. 24, No. 3, pp. 491-495.
"Sulforaphane Glucosinolate Monograph", Alternative Medicine Review, 2010, vol. 15., No. 4, pp. 352-360.
Song, et al., "Purification of Major Glucosinolates From Bassicaceae Seeds and Preparation of Isothiocyanate and Amine Metabolites", Journal of Science and Food Agrlculture, 2006, vol. 86, pp. 1271-1280.
Szmigielska, A., et al., "Determination of Gluscosinolates in Canola Seeds Using Anton Exchange Membrane Extraction Combined with the High-Pressure Liquid Chromatography Detection". Journal of Agricultural Food and Chemical, 2000, vol. 48(10), pp. 4487-4491.
Thomson, C., et al., "Chapter 15: Cruciferous Vegetables and Cancer Prevention", Functional Foods & Nutraceuticals in Cancer Prevention, R. Watson, 2003, pp. 263, 269-270.

(56) References Cited

OTHER PUBLICATIONS

Traka, M., et al., "Glucosinolates, isthiocyanates and human health", Phytochem Rev., 2009, pp. 8:269-282.

Troyer, et al. "Analysis of Glusosinolates from Broccoli and Other Cruciferous Vegetables by Hydrophilic Interaction Liquid Chromatography", Journal of Chromatography A, 2001, vol. 919, pp. 299-304.

Vallejo, F., et al., "Potential Bioactive Compounds in Health Promotion From Broccoli Cultivars Grown in Spain." Journal of the Science of Food and Agriculture, vol. 82, No. 11, Sep. 2002, pp. 1293-1297.

Vallejo, F., et al., "Total and Individual Glucosinolate Contents in Inflorescences of Eight Broccoli Cultivars Grown Under Various Climatic and Fertilization Conditions," Journal of the Science of Food and Agriculture, vol. 83, No. 4, Mar. 2006, pp. 307-313.

VanEtten, C.H., et al., "Glucosinolate Determination in Cruciferous Seeds and Meals by Measurement of Enzymatically Released Glucose," Journal of Agricultural and Food Chemistry, vol. 22, No. 3, 1974, pp. 483-487.

VanEtten, C., et al., "Glucosinolates in Cruciferous Plants", Effects of Poisonous Plants on Livestock, 1978, pp. 507-520.

VanEylen, D., et al., "Behavior of mustard seed (*Sinapis alba* L.) myrosinase during temperature/pressure treatments: a case study on enzyme activity and stability", European Food Research and Technology A, 2008, vol. 226, pp. 545-553.

Visvanathan, K., et al., "Preclinical and Clinical Evaluation of Sulforaphane for Chemoprevetion in the Breast", Carcinogenesis Advance Access, Mar. 7, 2007.

Wang, M., et al., "Preparation and Functional Properties of Rice Bran Protein Isolate", Journal of Agricultural Food & Chemistry, 1999, vol. 47, pp. 411-416.

West, L., et al., "Glucoraphanin and 4-Hydroxyglucobrassicin Contents in Seeds of 59 Cultivars of Broccoli, Raab, Kohlrabi, Cauliflower, Brussels Sprouts, Kale, and Cabbage," Journal of Agricultural and Food Chemistry, col. 52, No. 4, 2004, pp. 916-926.

West, L., et al., "Single Column Approach for the Liquid Chromatographic Separation of Polar and Non-Polar Glucosinolates from Broccoli Sprouts and Seeds," Journal of Chromatography A, 2002, 966, pp. 227-232.

Zrybko, et al., "Determination of glucosinolates in domestic and wild mustard by high-performance liquid chromatography with confirmation by electrospray mass spectrometry and photodiodearray detection." Journal of Chromatography A., 1997, vol. 767, pp. 43-52.

European Extended Search, European Patent Application No. 08104379.6, date of completion of search Jul. 21, 2011, 6 pages.

International Search Report dated Dec. 16, 1998 for Application No. PCT/GB98/02370.

International Search Report dated Jul. 17, 2006 for Application No. PCT/US06/10032.

Merriam-Webster's Collegiate Dictionary, 11$^{th}$ ed., ed., Merriam-Webster's Inc., 2004, pp. 1-20.

* cited by examiner

SPRAY DRIED MYROSINASE AND USE TO PRODUCE ISOTHIOCYNATES

CROSS REFERENCE TO RELATED APPLICATIONS

The present application hereby claims the benefit of the provisional patent application Ser. No. 61/445,156, filed on Feb. 22, 2011, the disclosure of which is hereby incorporated by reference in its entirety.

BACKGROUND

Numerous studies have shown that eating certain vegetables, particularly cruciferous vegetables, may reduce one's risk of developing cancer. The origin of this chemoprotective effect is generally attributed to glucosinolates in the vegetables that are converted into isothiocyanates by contact with endogenous myrosinase enzymes when plant cell walls are breached. Some of these isothiocyanates have been shown to be potent Phase II enzyme inducers, which can protect cells against the toxic and neoplastic effects of carcinogens.

Myrosinase catalyzes the conversion of glucosinolates to isothiocyanates. The rate and yield of the isothiocyanates may be altered by the source and quality of the myrosinase. One well known isothiocyanate is sulforaphane.

Glucosinolates may be converted to isothiocyanates through the use of myrosinase enzymes. However, during conversion other products may be formed which decreases the amount and purity of isothiocyanates produced.

BRIEF SUMMARY

A spray dried myrosinase/ascorbate mixture is formed from the steps comprising: providing a source of myrosinase, adding ascorbate to the source of myrosinase to produce a mixture, heating the mixture in a solvent to a temperature of about 104° F. (about 40° C.) or higher, and spray drying the myrosinase/ascorbate mixture.

In one embodiment, a process for producing spray dried myrosinase/ascorbate mixture comprises the steps of: providing a source of myrosinase, adding ascorbate to the source of myrosinase to produce a myrosinase/ascorbate mixture, heating the mixture in a solvent to a temperature of about 104° F. (about 40° C.) or higher, and spray drying the myrosinase/ascorbate mixture.

In one embodiment, a process for producing isothiocyanates comprises mixing plant material comprising glucosinolates; spray dried myrosinase/ascorbate mixture; and ascorbate in water at a pH of from about 5 to about 6.5.

An activated tablet or capsule comprises a spray dried myrosinase/ascorbate mixture and glucoraphanin.

DETAILED DESCRIPTION

Glucosinolates can be catalytically converted to isothiocyanates by the enzyme myrosinase. Both glucosinolates and myrosinase may be found in many crucifers and are generally higher in concentration in the sprouts and seeds than in the rest of the plant. A well known isothiocyanate is sulforaphane, which is a potent inducer of mammalian detoxification and chemoprotection by inducing Phase 2 enzymatic activity. Glucoraphanin, a glucosinolate, is the precursor to sulforaphane.

The yield of sulforaphane from glucoraphanin is reduced by epithiospecifier protein (ESP), which is also present in crucifers with myrosinase. ESP catalyzes the formation of sulforaphane nitrile; this alternative reaction pathway competes with the reaction pathway that creates sulforaphane. One way to deactivate ESP is through heating.

In one embodiment, a spray dried myrosinase/ascorbate mixture is made by mixing a source of myrosinase with ascorbate and heating the mixture to a temperature of about 104° F. (about 40° C.) or higher, and then spray drying the mixture. The resulting spray dried myrosinase/ascorbate mixture has improved properties over other myrosinase. It is more stable; in addition it is more active in producing sulforaphane from glucoraphanin Spray dried myrosinase/ascorbate mixture may have an improved yield of sulforaphane, may produce sulforaphane at a more rapid rate, or both.

In another embodiment the source of myrosinase is heated to a temperature of about 104° F. (about 40° C.) or higher, then mixed with ascorbate, heated to a temperature of about 95° F. (35° C.) or more, and then spray dried. After the ascorbate and the source of myrosinase have been mixed, the mixture may be incubated before it is spray dried.

A source of myrosinase may be from a cruciferous plant, such as daikon radish, broccoli, and rapeseed. In one embodiment the source of myrosinase may be the seeds, florets, or sprouts of a cruciferous plant. In another embodiment the source of myrosinase may be a broccoli plant. In another embodiment the source of myrosinase may be the seeds of a broccoli plant. The seeds of a broccoli plant may be processed by grinding it into a powder. In another embodiment, the seeds may be crushed or otherwise processed to crack or remove the hull.

Ascorbate is defined as salts of ascorbic acid. Examples of ascorbate include calcium ascorbate, sodium ascorbate, potassium ascorbate, and magnesium ascorbate. In one embodiment the ascorbate used in the formation of spray dried myrosinase is calcium ascorbate. The amount of ascorbate need not be enough to alter the pH of the aqueous solution. In one embodiment the amount of ascorbate is about 5 grams per 10 L of water. In another embodiment the amount of ascorbate is about 1 to about 5 grams per 10 L of water. In another embodiment the amount of ascorbate may be from about 1 to about 10 grams, about 2 to about 10 grams, or about 3 to about 12 grams per 10 L of water. In one embodiment broccoli seed meal is mixed with calcium ascorbate in water. The mixture is heated to a temperature of about 104° F. (about 40° C.) or higher, and then spray dried.

The source of myrosinase is heated. Typically the myrosinase is heated to a temperature range of about 104° F. (about 40° C.) or higher. In one embodiment, the myrosinase is heated to about 104° F. to about 225° F. (about 40° C. to about 107° C.); about 110° F. to about 220° F. (about 43° C. to about 104° C.); about 120° F. to about 190° F. (about 49° C. to about 88° C.); about 130° F. to about 180° F. (about 54° C. to about 82° C.); about 135° F. to about 175° F. (about 57° C. to about 79° C.); about 140° F. to about 175° F. (about 60° C. to about 79° C.); about 145° F. to about 175° F. (about 82° C. to about 79° C.); about 150° F. to about 175° F. (about 66° C. to about 79° C.); about 155° F. to about 175° F. (about 68° C. to about 79° C.); about 160° F. to about 175° F. (about 71° C. to about 79° C.); about 164° F. to about 175° F. (about 73° C. to about 79° C.); or about 164° F. (about 73° C.).

Upon heating the source of myrosinase the ESP is believed to be deactivated. Less time is required at a higher temperature; more time is required at a lower temperature. In one embodiment, the source of myrosinase is heated for about 1 minute or more. It may be heated about 2 minutes or more, 3 minutes or more, 4 minutes or more, 5 minutes or more, 6 minutes or more, 7 minutes or more, or 10 minutes or more.

The source of the myrosinase and ascorbate may be heated in an aqueous solution. The pH of the aqueous mixture of the source of myrosinase and ascorbate is typically initially between about 4.5 to about 7.5. In one embodiment the pH range is from about 5 to about 7.5, about 5.5 to about 7.5, about 5.5 to about 7.0, about 6.0 to about 7.0, or about 5.0 to about 6.0. After the mixture has been in the aqueous solution the pH may change.

In one embodiment the heat treated myrosinase/ascorbate mixture in an aqueous solution is separated from the seed meal or other plant material. In another embodiment the myrosinase may also be filtered. The solution containing myrosinase/ascorbate mixture is then spray dried. In another embodiment, there is no need to separate the myrosinase/ascorbate mixture from the seed meal or other plant material, instead it is spray dried homogeneously. In one embodiment, the myrosinase/ascorbate mixture and the seed meal or other plant material is homogenized then spray dried. In another embodiment the myrosinase/ascorbate mixture and the seed meal or other plant material is sonicated then spray dried.

The myrosinase/ascorbate mixture may be mixed with a starch material before spray drying. Examples of starch materials are cyclodextrin, maltodextrin, sucrose, dextrose, corn starch, and vegetable gums. The amount of starch material may be about 10% by weight. The temperature of the air the myrosinase/ascorbate mixture is sprayed into may be from about 180° F. to about 215° F. The method of spray drying is well known to a person of ordinary skill in the art. Typically the material to be spray dried must be dissolved, suspended, or otherwise in a solution. If the heating steps were not performed with the source of myrosinase in a solution, a liquid must be added before the spray drying step.

Isothiocyanates, such as sulforaphane, may be produced from plant material containing glucosinolates. In one embodiment the source of glucosinolates is glucoraphanin, which can be produced by any method known in the art including the method described in U.S. Publication No. 2009/0081138, which is herein incorporated by reference in its entirety. Other sources of glucosinolates are other crucifer plants, such as cabbage, kale, cauliflower, broccoli, mustard greens, kohlrabi, brussels sprouts, turnips and horseradish root. Typically the sprouts and seeds contain the most glucosinolates, but other parts of the plants may be used.

In one embodiment glucosinolate and the spray dried myrosinase/ascorbate mixture are mixed together in water. The mixture may be heated above 95° F. for at least 1 minute. The mixture may be heated for about 70 to 100 minutes. The rate of conversion of glucosinolate to isothiocyanate depends upon the temperature. At a lower temperature the conversion may take longer, at a higher temperature the conversion will take less time. There is no requirement that the mixture be heated above 95° F. This procedure may be used to convert various glucosinolates to isothiocyanates, such as glucoraphanin to sulforaphane.

Various solvents may be used for the conversion process. In one embodiment the solvent for the glucosinolate and the spray dried myrosinase/ascorbate mixture is distilled or deionized water because it is substantially free from iron or zinc ions. In another embodiment the water is not distilled or deionized. In another embodiment, the solvent may be an aqueous solution which comprises water.

In one embodiment the initial pH of the glucosinolate and the spray dried myrosinase/ascorbate mixture is about 5 to about 6.5. In one embodiment the pH range is from about 5 to about 7.5, about 5.5 to about 7.5, about 5.5 to about 7.0, about 6.0 to about 7.0, or about 5.0 to about 6.0. After the mixture has been in the aqueous solution the pH may change.

In one embodiment the mixture of a source of glucoraphanin and the spray dried myrosinase additionally comprises ascorbate. In one embodiment the amount of ascorbate may be from about 0.1% to about 2%, about 0.5% to about 1.5%, or about 1% by weight.

After the conversion of glucosinolates to isothiocyanate the solution of isothiocyanates may be spray dried.

An activated tablet or capsule may comprise the spray dried myrosinase/ascorbate mixture and a glucosinolate, such as glucoraphanin. Glucoraphanin can be converted to sulforaphane by some people in their intestinal tract, however not all people are able to do this efficiently. A tablet or capsule containing myrosinase and glucoraphanin can be used to convert glucoraphanin to sulforaphane in vivo. This will provide a more certain and consistent dosage of sulforaphane. Sulforaphane is less stable than glucoraphanin and myrosinase, and will decompose. So, a tablet or capsule containing a spray dried myrosinase/ascorbate mixture and that produces sulforaphane in vivo will have a longer shelf life than a tablet or capsule containing sulforaphane.

The tablet or capsule may also comprise ascorbate. In one embodiment the tablet or capsule comprises a mixture of ascorbate, glucoraphanin, and spray dried myrosinase/ascorbate mixture that can produce about 12 to about 20 μmoles of sulforaphane in 2-3 hours. A tablet of this composition is able to produce a fixed dosage of sulforaphane. The amount of sulforaphane produced in vivo will depend upon the amount of glucoraphanin used in the tablet or capsule. In one embodiment, the tablet or capsule comprises about 100 mg of glucoraphanin. The mixture of ascorbate, glucoraphanin, and spray dried myrosinase/ascorbate mixture used in the tablet or capsule may be mixed in a ratio of 1 g of ascorbate, 7.5 g of spray dried myrosinase/ascorbate mixture, and 100 g of glucoraphanin. The ratio of the ingredients may be varied.

To allow the tablet to pass through the intestinal tract to the small intestine, an enteric coating may be formed over the tablet. In another embodiment the tablet may have a time release coating or controlled-release coating. Spray dried myrosinase/ascorbate mixture and glucoraphanin particles may be separately or as a mixture coated with enteric coatings. Use of enteric coatings, time release coatings and controlled-release coatings are well known. An enteric coating releases the contents to the intestine. In another embodiment, a capsule may be used. The spray dried myrosinase, glucoraphanin, and the ascorbate may be coated with an enteric coating within the capsule.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

Example 1

(Spray Dried Myrosinase)

Broccoli seed (200 g) containing myrosinase was milled to a powder. The powdered seed was mixed with distilled water (200 mL) at 95° F. (35° C.). The mixture was rapidly mixed for 5 minutes, then heated to 165-175° F. (74° C.-79° C.) and held at that temperature for 5 minutes. Calcium ascorbate (10 mg) was added to the mixture, which was then incubated for 24 hours at 98° F. (37° C.). The mixture was strained and the liquid homogenized. The homogenized liquid was then spray dried.

Example 2

(Convert Glucoraphanin to Sulforaphane)

Broccoli seeds containing high levels of glucoraphanin (sulforaphane glucosinolate) were crushed in an extruder at 270° F. (132° C.). The crushed seed was defatted by means of super critical extraction using super critical $CO_2$ to produce glucoraphanin powder.

Spray dried myrosinase/ascorbate mixture (100 mg) from Example 1, glucoraphanin powder (1 g, 130 μm glucoraphanin/g), and calcium ascorbate (10 mg) were mixed together in distilled water (500 mL) at 99.5° F. (37.5° C.). After 70 to 100 minutes the liquid was filtered, and spray dried to produce sulforaphane (62 μm).

Example 3

Broccoli seeds, which contain glucoraphanin (sulforaphane glucosinolate), were crushed in an extruder at 270° F. (132° C.). The crushed seed was defatted by means of super critical extraction using super critical $CO_2$. Water was added to the seed meal (5:1 water:seed meal).

A source of myrosinase enzyme, broccoli seed, was milled. The milled seed was hydrated in water (5:1 water: milled seed by weight). The mixture was heated to 135° F.-145° F. (57° C.-63° C.) for 3-5 minutes, then cooled to around 90° F. Ascorbate (0.01 g/g milled seed meal) was added to the hydrated milled seed. The pH of this mixture was about 5.9 to 6.1. The mixture was allowed to incubate for 24 hours at 99.5° F. (37.5° C.).

The myrosinase mixture was added to the glucoraphanin mixture (1:100 myrosinase:glucoraphanin by weight) at 99.5° F. (37.5° C.). After 70 to 100 minutes the liquid is filtered, and spray dried to produce sulforaphane.

Example 4

Glucoraphanin powder and deionized water (1:5 to 1:10 weight ratio) were mixed at a temperature of 135° F. for 15 minutes. The mixture was cooled to 95° F.-100° F. (35° C.-38° C.) and calcium ascorbate (0.01:1 of ascorbate to myrosinase by weight) was added to the mixture. Spray dried myrosinase/ascorbate mixture (0.1:1 of myrosinase to glucoraphanin by weight) from Example 1 was added to the mixture and incubated at 95° F.-100° F. (35° C.-38° C.) for 1 hour.

Example 5

(Spray Dried Myrosinase)

Broccoli seed (100 g) was ground and added to distilled water (10 L) at 73° C. (164° F.). Ascorbate (5 g) was added and the mixture was stirred for 7 minutes then cooled. The mixture was kept at 35° C. (95° F.) for 24 hours. The liquid was decanted and spray dried with 10% by weight maltodextrin. Four samples were made using this procedure. The ascorbate used is shown in the table below. Sample 3 was decanted after the mixture was cooled; unlike the other samples, it was not kept at 35° C. (95° F.) for 24 hours. All the samples of spray dried myrosinase were tested for the rate and amount of sulforaphane they were able to produce; see the table below. A sample of 1 gram was tested from a mixture of ascorbate (1 g), spray dried myrosinase (7.5 g), and glucoraphanin (100 g).

The spray dried myrosinase/ascorbate was able to produce sulforaphane more rapidly than spray dried myrosinase. See Samples 1 and 3, which at three hours produced 30.2 and 47.7 μmol sulforaphane, respectively. These Samples generated more sulforaphane at three hours in comparison to myrosinase that was not mixed with ascorbate (25.2 μmol sulforaphane) and myrosinase that was mixed with ascorbic acid (20.79 μmol sulforaphane). A rapid generation of sulforaphane in three hours is more important than an overall yield because the glucoraphanin will not remain in the gastrointestinal tract for 24 hours, when the complete conversion of glucoraphanin to sulforaphane has taken place.

| Making the Spray Dried Myrosinase | | | | |
|---|---|---|---|---|
| Sample | Ascorbate | Initial pH | pH after stirring | pH after 24 h |
| 1 | calcium ascorbate | 6.3 | 5.43 | 5.66 |
| 2 | ascorbic acid | 6.3 | 5.33 | 5.54 |
| 3 | calcium ascorbate | 6.2 | 4.82 | — |
| 4 | — | 6.3 | 5 | 4.6 |

| Testing the Spray Dried Myrosinase | | | | | | |
|---|---|---|---|---|---|---|
| Sample | Initial pH | pH at 1 h | sulforaphane at 1 h (μmol) | pH at 3 h | sulforaphane at 3 h (μmol) | pH at 24 h | sulforaphane at 24 h (μmol) |
| 1 | 5.3 | 5.3 | 12.4 | 5.2 | 30.2 | 4.8 | 83 |
| 2 | 5.3 | 5.3 | 11 | 5.2 | 20.79 | 4.5 | 83.6 |
| 3 | 5.4 | 5.2 | 20 | 5 | 47.7 | 4.5 | 87 |
| 4 | 5.3 | 5.21 | 17 | 5.21 | 25.2 | 4.86 | 85.3 |

What is claimed is:

1. A process for producing spray dried myrosinase and ascorbate mixture consisting of the steps of:
   providing a source of myrosinase, wherein the source of myrosinase is broccoli seeds;
   adding the source of myrosinase to water;
   heating the source of myrosinase to a first temperature, wherein the first temperature is at least 104° F.;
   adding 0.1% to 2% by weight ascorbate to the source of myrosinase;
   heating the myrosinase and ascorbate mixture to a second temperature, wherein the second temperature is at least 95° F., the second temperature being lower than the first temperature; and filtering and spray drying the myrosinase and ascorbate mixture after the heating steps.

2. The method of claim 1, wherein the spray drying occurs at an air temperature from 180° F. to 215° F.

3. The method of claim 1, wherein the heating the source of myrosinase to a first temperature occurs for a first duration, wherein the heating the source of myrosinase to a second temperature occurs for a second duration, and wherein the second duration is longer than the first duration.

4. The method of claim 3, wherein the first duration is at least 1 minute.

* * * * *